United States Patent [19]

Bartholomew

[11] Patent Number: 4,802,947
[45] Date of Patent: Feb. 7, 1989

[54] APPARATUS FOR ATTACHING A CATHETER TO A HUB

[75] Inventor: Victor L. Bartholomew, Sandy, Utah

[73] Assignee: Becton Dickinson and Company, Franklin Lakes, N.J.

[21] Appl. No.: 887,004

[22] Filed: Jul. 16, 1986

[51] Int. Cl.⁴ .................... B29C 57/06; B29C 65/04; B32B 31/20

[52] U.S. Cl. .................. 156/380.5; 156/380.6; 156/380.8

[58] Field of Search ............... 264/248, 292, 159, 274; 156/73.1, 272.9, 273.7, 274.4, 275, 294, 303.1, 308.1, 308.4, 309.6, 380.2, 380.5, 380.6, 380.8, 443; 604/283, 165, 167

[56] References Cited

U.S. PATENT DOCUMENTS

| | | | |
|---|---|---|---|
| 2,974,367 | 3/1961 | Doering | 156/294 |
| 3,322,590 | 5/1967 | Clark | 156/294 |
| 3,558,397 | 1/1971 | Clark | 156/290 |
| 4,409,046 | 10/1983 | Holzwarth | 156/294 |

Primary Examiner—Merrell C. Cashion, Jr.
Attorney, Agent, or Firm—Aaron Passman

[57] ABSTRACT

Disclosed is a piece of equipment, a method, and a product resulting from the attachment of a hub and a catheter. The transition between the catheter and hub are a smooth funnel-like flare of the distal end of the small diameter thin wall catheter into the open inside chamber of the catheter attachment hub. The hub is used to connect an administration set to the catheter. In the method, a probe is used which has a flared transition that is urged into the distal end of the small diameter catheter to flare same outwardly and against the inside proximal end of the catheter hub chamber. The probe is one source of dielectric welding energy and there is a support for completing this circuit. During the imposition of dielectric welding energy, the flared small diameter catheter end is melted, extruded, fused, and tapered in a molding operation into the inner proximal end wall of the catheter hub chamber.

3 Claims, 2 Drawing Sheets

APPARATUS FOR ATTACHING A CATHETER TO A HUB

BACKGROUND OF THE INVENTION

This invention relates to the connection between the thin-walled small diameter catheter for insertion into the lumen of a human and its respective attachment hub with a larger inside diameter. The hub is made with a luer thread to connect to the supply for the administration fluid. More specifically, the disclosure relates to a unique dielectric welding attachment between the catheter and hub which attachment forms a fluid tight connection to prevent leakage or turbulence of the flow of fluid through the hub and into the smaller diameter of the catheter.

In the past, prior patents have disclosed techniques for connecting catheter tubing to hubs. One such U.S. Pat. No. 4,354,495 shows an injection molding operation used to attach the hub to the catheter. The distal end of the catheter has a thread-like configuration induced by heating and swelling the catheter at its distal end to form the helix of the thread. This thread-like member is used as a situs about which the injection molded hub can adhere. This connection is primarily mechanical. The internal juncture in bore and between the proximal end of the catheter and the distal end of the hub are not smooth and do not form a smooth transition for the flow of the administrated fluid.

U.S. Pat. No. 4,177,809 shows a three-piece configuration for mounting the catheter to the hub. The distal end of the catheter is surrounded by a funnel-shaped wedge inserted between it and the inside diameter of the hub to act as a key or keeper to retain the catheter in its axial position relative to the hub. This force fit is merely mechanical. Even though the wedge has a funnel-like interior, there is still a shoulder between it and the inside diameter of the hub and there is absolutely no teaching of welding.

U.S. Pat. No. 3,720,210 shows another way of flanging the distal end of the catheter with a curl in order to form a place at which an insert molded hub can be affixed without concern for the two separating from one another. The connection is mechanical.

U.S. Pat. No. 4,419,095 discloses RF heating to butt weld the ends of two tubes together. The outside mandrel has a convex surface in order to allow air to escape therefrom during welding. There is also a recess along the outside wall of an end of one of the tubes in order to facilitate the removal of air. The inside mandrel has an insulated sleeve over it to facilitate the weld and prevent the inside of the tube from sticking to the inside mandrel. There is absolutely no teaching of changing the overall configuration of the two tubes during the welding process. The process is merely designed to melt the tubing at the interface.

U.S. Pat. No. 3,966,520 shows ultrasonic welding as opposed to RF welding wherein a conically-shaped tool surrounds the ends of one tube that extends over in a lap joint about another tube. Ultrasonic vibrations in the frequency range of 20 to 40 kHz are used during swaging the outer tube toward the underlapping inner tube and in doing so tends to chamfer the leading end of the outer overlapping tube. The internal juncture between the tubes has the same configuration with a shoulder, there is no smooth transition between them even though an inside mandrel is used to support the overlapped tubing during the ultrasonic vibration forming operation.

U.S. Pat. No. 4,430,083 is typical of state of the art prior patents in that it shows a catheter receiving hub wherein there is an enlarged recess to receive the catheter such that the flow through the inside of the passageway through the tube is uniform. This requires that the hub be molded from both directions and a split set of core pins be used. This approach, while possible, does not afford the best possible fused junction between the hub inside diameter passage and the thin walled small catheter bore and may leave flash at the site where the core pins meet.

Therefore, it is an object of the present invention to provide a juncture between the hub and the catheter which forms a smooth, funnel-like transition from the larger inside diameter of the hub to the smaller inside bore of the catheter with no discontinuity along the wall to affect the flow of fluid therethrough.

It is a further object of the present invention and the preferred embodiment to disclose a quick, efficient means by which the distal end of the catheter and the proximal end of the hub can be joined together using dielectric welding leaving a clean internal connection therebetween without excess adhesives, flash from molding operations or additional component parts to wedge and force-fit the two together.

Consistent with the foregoing objects and in order to overcome the problems besetting the prior art, the present disclosure which follows seeks to disclose and explain a preferred embodiment in which the connection between the distal end of the catheter and the proximal end of the hub form a clean, continuous fluid tight internal junction having a smooth transition from the larger diameter of the inside of the hub to the smaller diameter of the inside of the catheter.

SUMMARY OF THE INVENTION

The relatively simple and desired result of a technique, product and method for joining a elongated, thin-walled, hollow, tubular catheter having a taper at its proximal end and a flanged juncture at its distal end to the inside end of a hub for facilitating connection of the catheter to an administration set is disclosed. More specifically, the hub has a relatively thick wall tubular body with an internal chamber tapering from a larger diameter at the distal end to a smaller internal diameter at the proximal end which internal diameter is equal to the outer diameter of the distal end of the catheter. Proximal and distal are used here in relation to the patient. The tapered hollow chamber within the hub has a portion for receiving the distal end of the catheter during a dielectric welding, fusing and extrusion molding operation. In particular, the catheter is coaxially placed upon a probe which has a minor diameter and a major diameter with a shoulder transition therebetween. The catheter is slid coaxially about the minor diameter of the probe with its proximal end biased toward the wedge-like transition to open the catheter end into a funnel shape. Over the catheter and coaxially thereabout is slid a hub which is supported upon the major diameter of the probe and in coaxial alignment with the catheter such that the inside of the proximal end of the hub surrounds the funnel shaped distal end of the catheter as same rests against the wedge-like transition of the probe.

The catheter being biased against the flared wedge-like transition, the hub being located and held relative to the distal end of the catheter and the probe being urged toward the catheter whereby the internal diameter of the catheter at its distal end is forced onto the flared transition as dielectric energy is applied causing the polymeric material of the catheter and hub to melt, extrude and fuse. The pressure of the probe, the biasing of the catheter, and the positioning of the hub cause the catheter material to extrude and intimately fuse with the internal material of the hub there adjacent. This extruding fusing process forms a funnel-like opening at the distal end of the catheter which provides a smooth relatively feather-edged transition from the chamber of the hub into the inner diameter of the catheter bore.

The resulting product is a relatively thick-walled hub which is easy to handle and connect to an administration set with a fluid-tight, funnel-like juncture into a relatively thin wall catheter bore. There are no extraneous adhesives, cements or bonding agents between the catheter and the hub at and around the juncture. In addition, there are no areas of flash due to the unique nature of the molding operation employed.

DETAILED DESCRIPTION OF THE DRAWINGS

Figure 1:
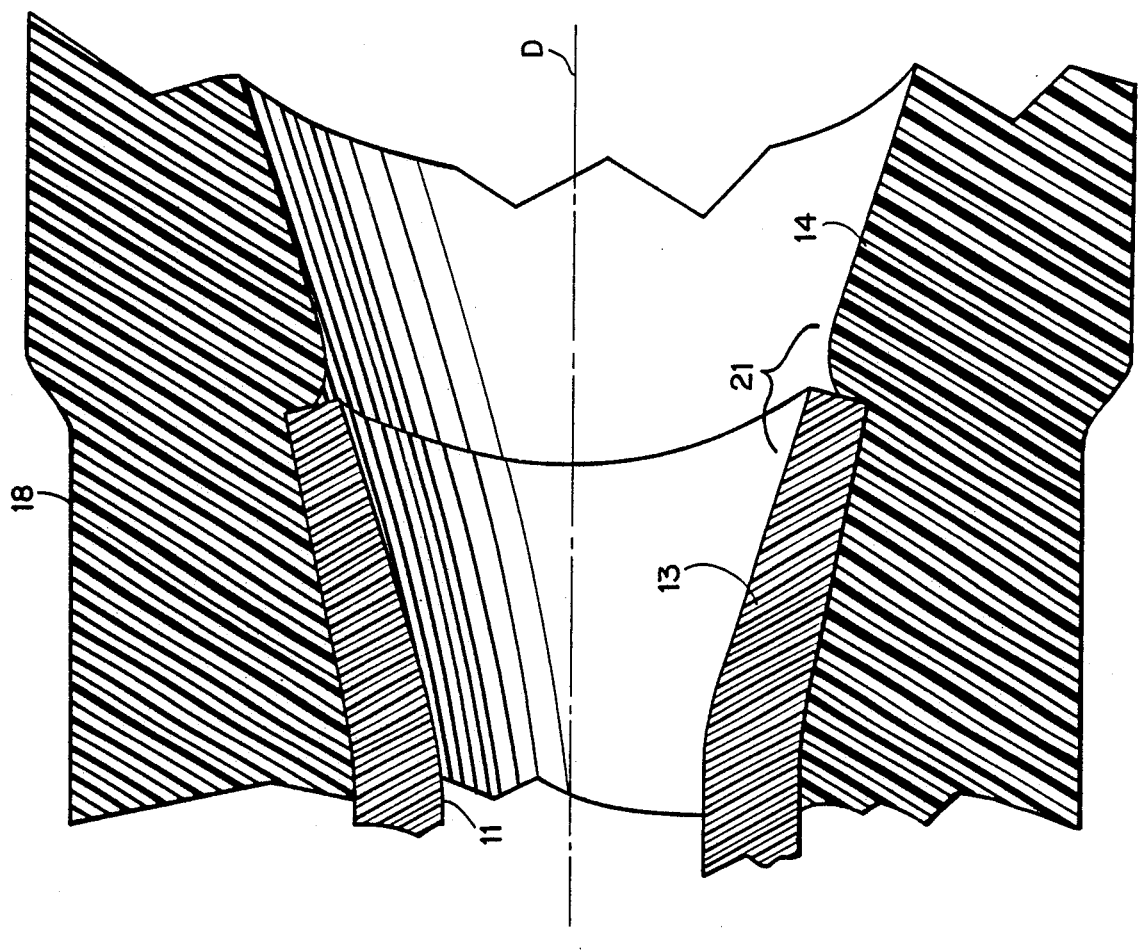
FIG. 1 is an enlarged cross-sectional view of the juncture between the catheter and the hub showing the nature of the flared funnel-like transition formed at the proximal end of the catheter where same is molded and fused into the internal wall of the hub.
Figure 2:
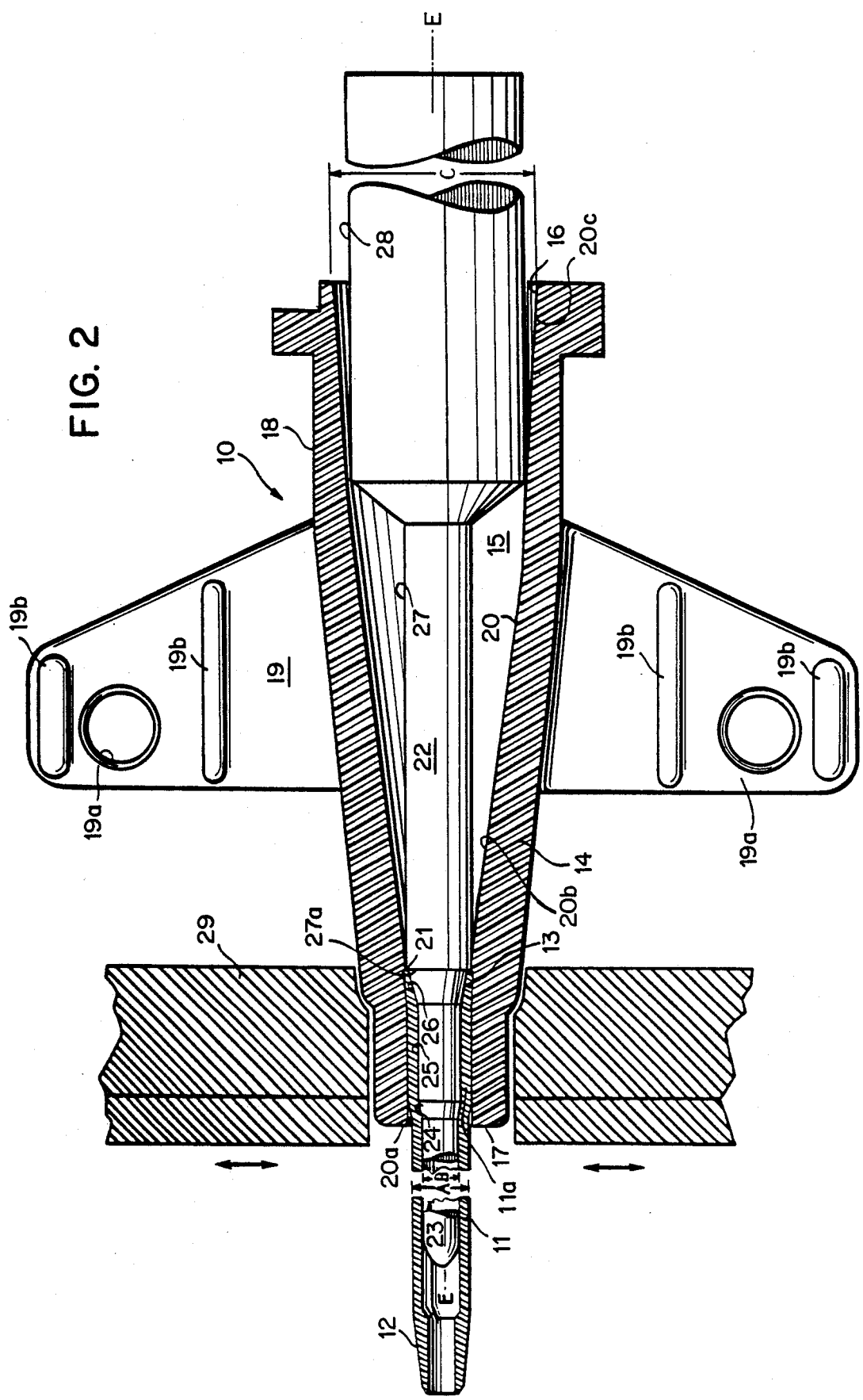
FIG. 2 shows the probe placed within the crosssectional view of the catheter and hub such as would occur during the molding, extruding and fusing operation.

Turning now to the figures and more specifically to FIGS. 1 and 2, there is shown the resulting juncture in the finished product, that is the fused, extruded, tapered, and molded catheter end and hub combination 10. The catheter 11 has a tapered proximal end 12 and a flared, tapered, molded, fused proximal end 13 with an outer diameter A and an inner or bore diameter B, FIG. 2. In combination with the catheter 11 is the hub 14 which includes tapered internal chamber 15 that extends from the distal end 16 to the proximal end 17 and reduces from a larger diameter C to a smaller diameter which is the same as A, the outer diameter of the catheter 11.

The hub 14 has a number of features which are incorporated to facilitate its use in connection to an administration set such as the luer thread on the outer body wall 18, and the tie-down wings 19 which includes suturing holes 19a and reinforcing ribs 19b. Each wing 19 extends transverse to the axis of the hub 14 designated D in FIG. 1 and of the axis of the probe designated E in FIG. 2. The internal wall 20 of chamber 15 has a proximal end portion 20a of the diameter slightly larger than A for receiving the distal end 11a of the catheter 11, FIG. 2. Extending distally from end portion 20a is a first outwardly tapering portion 20b which acts as the transition from diameter A toward larger internal diameter C. Wall portion 20b extends approximately to the distal portion of the juncture between the wings 19 and the hub body 14. From there an inside chamber wall 20c having a lesser angle relative to the axis E is provided and extends all the way to the distal end opening of the hub 14. Consequently, the chamber 15 is formed of three areas defined by walls 20a, 20b, and 20c extending from a minor proximal inside diameter A to a major distal inside diameter C.

The catheter 11 can have a variety of internal diameters which, for example, could extend from 0.017 to 0.0482 inches depending on the particular gauge and length of the catheter. The outer diameters all tend to be about the same for any given gauge and the wall thickness of the catheter tends to vary from 0.003 to 0.009 inches. Similarly, the hub 14 has a varying dimension for diameter A as a function of the particular gauge catheter which is inserted therein. It should be noted, however, that the relative wall thickness of the hub about the area at 11a is generally three to four times that of the wall thickness of the catheter such that the melting, fusing, extruding and molding operation is applied in such a way that the materials of different mass and relative thickness are melted uniformly and equally at their interface and throughout the flare so that same can be molded, extruded and fused to the hub to generate the desired flared funnel-like even end juncture generally shown in the area 21 in FIG. 1.

The preferred polymer for the catheter and the hub is a high dielectrically resistant material such that the energy applied to form the juncture at area 21 is efficiently used. In particular, dielectric bonding is a process wherein energy in the frequency range of 1 mHz to 1,000 mHz is used to excite the molecules in a polymeric material in such a fashion that the material melts at and around the interface between the component parts. This process can be localized to a large degree and has been used for welding conventional joints such as lap and butt.

In the preferred embodiment, the selected material is a filled polyurethane polar polymer and has a dielectric constant of about 4.4 but unfilled materials in the range of 3 to 10 for their dielectric constant have been found to work well. For purposes of biocompatibility in a medical device for use in connection with the human blood vessels, polyurethane is the preferred choice and more specifically, the polyurethane produced under the trademark VIALON® by Deseret Medical, Inc., Sandy, Utah. This material constant has been found to adapt well to the combined welding, fusing, extruding and molding operation described. The material difference between the catheter material and the hub is that the former may include a radiopaque stripe of barium ferrite; the latter does not. The addition of the radiopaque stripe does not affect the ability to obtain a fused juncture at area 21. One reason for this is the care with which the stripe has been buried within the basic polymeric, polyurethane VIALON® material used to form the catheter tubing. That is to say that, there is sufficient VIALON® polyurethane covering the stripe and available to form the juncture notwithstanding the addition of the radiopaque stripe. However, the dielectric constant is increased to some extent.

Turning now to FIG. 2, there is shown an elongated probe 22 used to support, hold and form the juncture at area 21 between the catheter 11 and the body of the hub 14. The proximal portion 23 of the probe 22 has an outer diameter of approximately B such that the catheter 11 can be coaxially positioned thereabout during the welding, fusing, extruding and molding operation. The length of portion 23 is, or course, a function of the particular catheter length and is also a function of the diameter B. More proximal than portion 23 is the transition flared portion 24 which has an angle of approximately 15 degrees relative to the axis E for the probe 22.

Transition flared portion 24 extends the diameter B outwardly very slightly to a land area 25 which is approximately 0.015 inches larger on the diameter than portion 23 for the purpose of expanding the catheter in the area of 11a so that same bears tightly against the inside of the hub 14 during assembly and RF heating, extruding, tapering, welding, and fusing. Intimate contact between the catheter and the hub are essential for providing the required drag or engagement during assembly to cause the hub to flare up about the transition so a complete and liquid-tight bond is thus formed.

More distal on probe 22 is a flare 26 at an angle of approximately 30 degrees to the axis E. Flare 26 connects the land area 25 to a hub extension 27 by means of a small radial shoulder 27a. The extension 27 has a diameter slightly smaller than the inside of the hub. The extension 27 reaches back to enlarged probe mandrel 28 of a diameter of approximately 0.125 inches which engages the inside of chamber 15 of the hub 14 and holds same coaxial with respect to the axis E of the probe 22 which in FIG. 2 is the same as axis D of the hub 14.

Therefore, during assembly the catheter 11 is inserted over the probe 22 first engaging end 23 and extending thereover such that portion 11a comes to bear against land area 25 and the distal portion thereof is up against flare 26. Thereover and being slid from the proximal end of catheter 11, the hub 14 is placed with its larger open end 16 first slid over the catheter 11 until the portion near proximal end 17 engages about the outer diameter A of the catheter 11, and more specifically, the surfaces 20a and 11a are brought into into engagement by the greater diameter of the land area 25 such that the probe 22 is biased into the catheter 11 as the hub 14 is pulled proximally against the catheter and the hub causing the area 13 on the catheter to be expanded and held tightly against the inside of the hub 14. The relative axial movement between the probe and catheter caused by the placement of the hub brings the distal end 13 of the catheter to bear against shoulder 27a. The dielectric energy then imposed through the probe across the juncture of the catheter 11 and the hub 14 causes the same to fuse at their interface and extrude and the melt catheter material at its proximal end into the inner surface of the hub 14 between the areas 20a and 20b. To provide a path for the dielectric energy, there is the grounding support 29 shown in FIG. 2 whereby the flow of power is between the probe and the support.

Turning now to FIG. 1, there is shown the area of the fused juncture 21 between the hub 14 and the catheter 11 and more specifically, the way in which the catheter material is tapered, flared and forced to fit against, into and within the inside wall of hub 14 such that a smooth transition between the inside diameter of the hub at its proximal end near juncture 21 with the distal end of the catheter 11 is generated. Clearly, the probe has tapered and recessed the catheter during the welding process.

Those skilled in the art will no doubt appreciate that changes in the angle, the relative size of the components, the materials and other dimensional and detail specifics of the configuration can be made without departing from the scope of the invention which is defined in the claims which follow.

What is claimed

1. A dielectric welding apparatus for use in coaxially supporting a catheter and its hub about an axis during an operation for expanding the bore of the catheter to the inside of the hub to form a flared smooth transition from the larger internal diameter of the hub to the smaller internal diameter of the catheter bore wherein the apparatus comprises:

an elongated probe located along the axis and having a minor diameter at its proximal end and said minor diameter extending axially for carrying and supporting the catheter along the axis and a major diameter at its distal end for carrying the hub in axial alignment with the catheter;

a portion on said elongated probe disposed between said minor diameter and said major diameter with at least a part thereof having a flared transition extending outwardly and distally of said minor diameter toward said major diameter for producing a funnel shaped distal end on the catheter when it is place axially over said minor diameter and biased axially up onto said flared transition, and said major diameter extending axially for cooperating with the inside of the hub when the hub is coaxially positioned about the catheter distal end to axially align the hub with respect to the catheter forming an interface between at least the funnel shaped distal end on the catheter and the inside wall of the hub; and a grounding support about the hub when positioned on said probe to receive dielectric energy across the interface between the catheter and hub and to carry the hub as said probe urges the catheter funnel shaped distal end into the inside wall of the hub.

2. The apparatus of claim 1 wherein said portion of said elongated probe includes a land area of a diameter slightly greater than said minor diameter which extends axially for expanding a length of the catheter proximal of the funnel shaped distal end to engage an additional part of the inside of the hub thereby extending the interface between catheter and hub.

3. The apparatus of claim 1 wherein said flared transition terminates distally in a shoulder extending outward of the distal end of said flared transition to prevent further axial distal movement of said catheter along said probe.

* * * * *